United States Patent
Peng

(10) Patent No.: US 10,039,934 B2
(45) Date of Patent: Aug. 7, 2018

(54) MULTI-WAVELENGTH INTERLEAVED OPTICAL STIMULATION

(71) Applicant: PHOTONEDGE INC., Pleasanton, CA (US)

(72) Inventor: Song Peng, Pleasanton, CA (US)

(*) Notice: Subject to any disclaimer, the term of this patent is extended or adjusted under 35 U.S.C. 154(b) by 0 days.

(21) Appl. No.: 14/585,030

(22) Filed: Dec. 29, 2014

(65) Prior Publication Data

US 2015/0184126 A1 Jul. 2, 2015

Related U.S. Application Data

(60) Provisional application No. 61/921,987, filed on Dec. 30, 2013.

(51) Int. Cl.
*A61N 5/06* (2006.01)
*A61B 18/20* (2006.01)

(52) U.S. Cl.
CPC ...... *A61N 5/0622* (2013.01); *A61B 2018/207* (2013.01)

(58) Field of Classification Search
CPC .......................... A61N 5/0622; C12N 2529/10
See application file for complete search history.

(56) References Cited

U.S. PATENT DOCUMENTS

| | | | | |
|---|---|---|---|---|
| 2003/0009103 A1* | 1/2003 | Yuste | ............ | A61B 5/0059 600/476 |
| 2004/0197771 A1* | 10/2004 | Powers | ............ | C12Q 1/04 435/5 |
| 2006/0018025 A1* | 1/2006 | Sharon | ............ | H04N 9/315 359/618 |
| 2006/0129210 A1* | 6/2006 | Cantin | ............ | A61N 1/372 607/88 |
| 2006/0221020 A1* | 10/2006 | Winer | ............ | G09G 3/2014 345/84 |
| 2007/0064228 A1* | 3/2007 | Tartakovsky | ............ | G01J 3/10 356/317 |
| 2007/0120786 A1* | 5/2007 | Bellls, II | ............ | G09G 3/3413 345/84 |

(Continued)

OTHER PUBLICATIONS

Johnstone et al. ("Functional Optical Imaging (FOI)," Dec. 3-4, 2011, pp. 1-2).*

(Continued)

*Primary Examiner* — Yubin Hung
(74) *Attorney, Agent, or Firm* — Dentons US LLP; Peter Su

(57) ABSTRACT

A method for driving an optical device for optical stimulation. In step (1) upon loading a first image pattern associated with light of a first wavelength into an SLM, the SLM is illuminated with light of the first wavelength for a first time period while the light of the second wavelength is off. In step (2) upon loading a second image pattern associated with light of a second wavelength into the SLM, the SLM is illuminated with light of the second wavelength for a second time period while the light of the first wavelength is off. The steps (1) and (2) are iteratively repeated, in that order, until a predetermined stimulation duration is attained. The first time period and the second time period are both shorter than a response time of a specimen (e.g., neuron(s)) that is being optically stimulated.

28 Claims, 4 Drawing Sheets

(56) References Cited

U.S. PATENT DOCUMENTS

| | | | | |
|---|---|---|---|---|
| 2008/0204665 A1* | 8/2008 | Cobb | H04N 9/315 | 353/31 |
| 2009/0033878 A1* | 2/2009 | Shirai | G02B 26/0841 | 353/37 |
| 2010/0150186 A1* | 6/2010 | Mizuuchi | H01S 3/09415 | 372/21 |
| 2010/0262212 A1* | 10/2010 | Shoham | A61N 5/0601 | 607/88 |
| 2011/0109958 A1* | 5/2011 | Yokoi | G02B 21/0032 | 359/363 |
| 2011/0125078 A1* | 5/2011 | Denison | A61N 5/0601 | 604/20 |
| 2011/0233046 A1* | 9/2011 | Nikolenko | G01N 21/6458 | 204/157.15 |
| 2012/0219021 A1* | 8/2012 | Lippey | H04N 9/3155 | 372/10 |
| 2012/0253261 A1* | 10/2012 | Poletto | A61M 5/14276 | 604/20 |
| 2013/0110236 A1* | 5/2013 | Nirenberg | A61F 9/08 | 623/6.63 |
| 2013/0144192 A1* | 6/2013 | Mischelevich | A61N 7/00 | 601/2 |
| 2013/0224821 A1* | 8/2013 | Deisseroth | G01N 33/5058 | 435/173.4 |
| 2013/0289669 A1* | 10/2013 | Deisseroth | A61K 48/005 | 607/88 |
| 2014/0142664 A1* | 5/2014 | Roukes | A61N 5/0622 | 607/88 |
| 2014/0268263 A1* | 9/2014 | Redford | G02B 21/06 | 359/10 |
| 2015/0246242 A1* | 9/2015 | Delp | A61N 1/0551 | 604/20 |
| 2016/0033874 A1* | 2/2016 | Tang | B29C 67/00 | 355/67 |

OTHER PUBLICATIONS

Baumgartner et al. ("Realization of an endoscope equipped with microprojection system for optogenetics," Proc. of SPIE, vol. 8225, 2012).*

Paralikar et al. ("An implantable 5mWchannel dual-wavelength optogenetic stimulator for therapeutic neuromodulation research," IEEE International Conference on Solid-State Circuits Conference Digest of Technical Papers (ISSCC), Feb. 7-11, 2010, pp. 238-239).*

Han et al. ("Multiple-color optical activation, silencing, and desynchronization of neural activity, with single-spike temporal resolution," PLoS ONE 2, e299, 2007).*

* cited by examiner

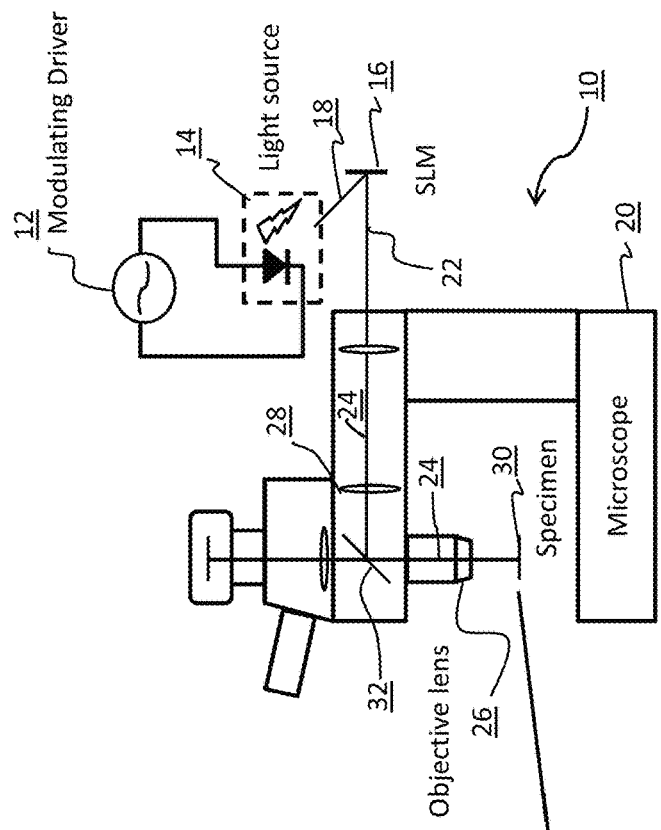
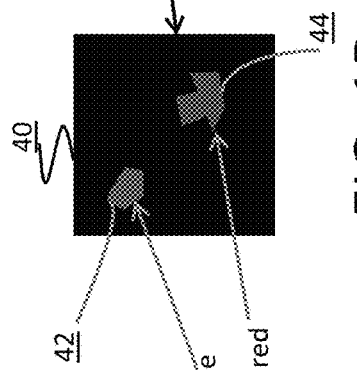
FIG. 1A
FIG. 1B

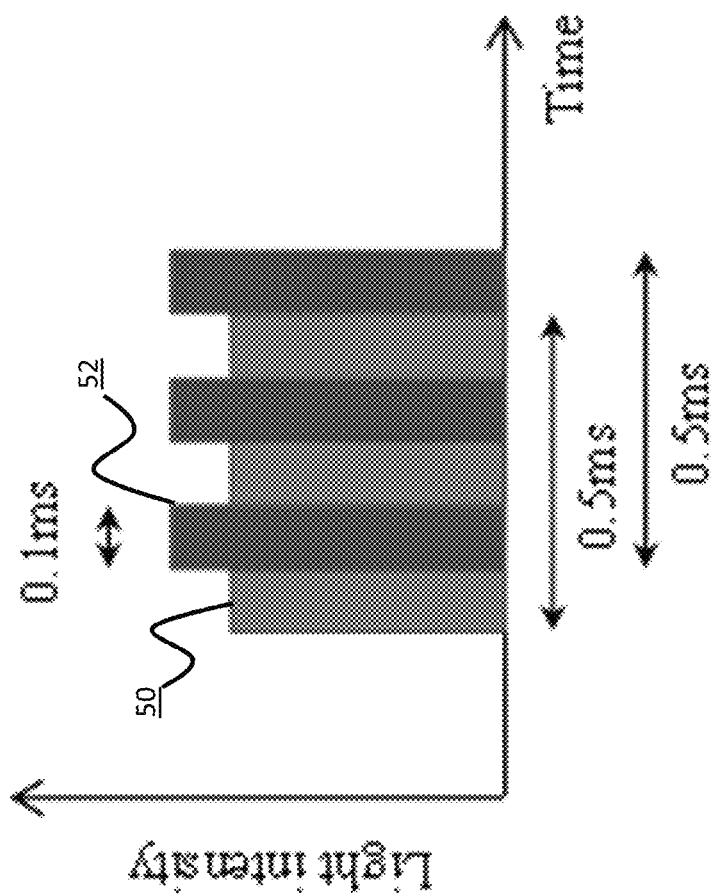

MULTI-WAVELENGTH INTERLEAVED OPTICAL STIMULATION

CROSS REFERENCE TO RELATED APPLICATIONS

The present application claims priority to U.S. Provisional Application Ser. No. 61/921,987, filed on Dec. 30, 2013, which is incorporated by reference herein in its entirety.

FIELD OF THE INVENTION

The present invention relates generally to a field of optics, and more particularly to a method of optically stimulating specimens with simultaneous multi-wavelength images.

BACKGROUND

Optogenetics and other applications often require two or more independent optical images of different wavelengths or colors to be simultaneously projected onto the same specimen to optically stimulate the specimen. As an example, in optogenetics research, a blue image can be used to excite certain neurons while an orange or red image can be used to inhibit some other neurons.

In general, a spatial light modulator ("SLM") may be used to generate an image to be projected onto a specimen. One conventional solution is to use multiple SLMs, where each generates an image of a single color, and then combine the images into a single image. An example of such a system is a three-panel color projector for display applications.

However, the use of a system having multiple SLMs has several drawbacks. Such system is expensive and requires a complex optical layout arrangement. Also, it is not particularly suitable for applications requiring a space-efficient compact design.

In addition, a conventional single-panel display system based on a field-sequential color, where, e.g., individual RGB images are displayed successively in a frame, operates at relatively low frequencies such as 60 Hz or 120 Hz. However, neuron responses are often faster than these low frequencies. For example, if colors were changed at a rate of 60 Hz or about every 17 ms, a typical neuron would be able to detect this 17 ms delay between colors. Therefore, a conventional single-panel display will introduce unwanted time dependence into experiments involving neurons.

SUMMARY OF THE INVENTION

The present disclosure provides an optical method that generates interleaved multi-wavelength images utilizing only a single SLM. The multi-wavelength images can be used to optically stimulate a specimen, such as neuron(s) or another biological specimen, since interleaving can be carried out in such a way that the images would appear to the specimen as being projected simultaneously for a duration of stimulation. Advantageously, with the benefit of the present disclosure, a single SLM can be used to produce an image of two independent colors, such as for optical stimulation of specimens.

In accordance with one disclosed embodiment, a method for driving an optical device for optical stimulation is provided. The method comprises the steps of (a) providing an image pattern $P_{\lambda 1}(i)$ associated with light of a first wavelength and an image pattern $P_{\lambda 2}(i)$ associated with light of a second wavelength to be loaded into an SLM, the first and second wavelengths being different from each other, and (b) providing a light source configured to output the light of the first wavelength and the light of the second wavelength.

The method further comprises the steps of (c) upon loading the image pattern $P_{\lambda 1}(i)$ into the SLM, illuminating the SLM with the light of the first wavelength at an intensity level $I_{\lambda 1}(i)$ for a time period $T_{\lambda 1}(i)$ before turning off the light of the first wavelength, the light of the second wavelength being in an off state during the time period $T_{\lambda 1}(i)$, and (d) upon loading the image pattern $P_{\lambda 2}(i)$ into the SLM, illuminating the SLM with the light of the second wavelength at an intensity level $I_{\lambda 2}(i)$ for a time period $T_{\lambda 2}(i)$ before turning off the light of the second wavelength, the light of the first wavelength being in an off state during the time period $T_{\lambda 2}(i)$. In the method, i is an integer number.

Further, in the disclosed method, the step (c) and the step (d) are iteratively repeated, in that order, until a predetermined stimulation duration is attained. Additionally, in accordance with the disclosed embodiment, each of the time period $T_{\lambda 1}(i)$ and the time period $T_{\lambda 2}(i)$ is shorter than a response time of a specimen that is being optically stimulated. Such specimen may include a neuron.

Additional features and advantages of embodiments will be set forth in the description, which follows, and in part will be apparent from the description. The objectives and other advantages of the invention will be realized and attained by the structure particularly pointed out in the example embodiments in the written description and claims hereof as well as the appended drawings. It is to be understood that both the foregoing general description and the following detailed description are illustrative and explanatory and are intended to provide further explanation of the invention as claimed.

BRIEF DESCRIPTION OF THE DRAWINGS

Various embodiments of the present invention are illustrated by way of example and are not limited to the following figures:

FIG. 1A illustrates an optical illumination system in which an illustrative embodiment can be carried out.

FIG. 1B illustrates an example of an output image containing images corresponding to two different wavelengths;

FIG. 2 illustrates one example of alternating light pulses;

DETAILED DESCRIPTION

Figure 3:
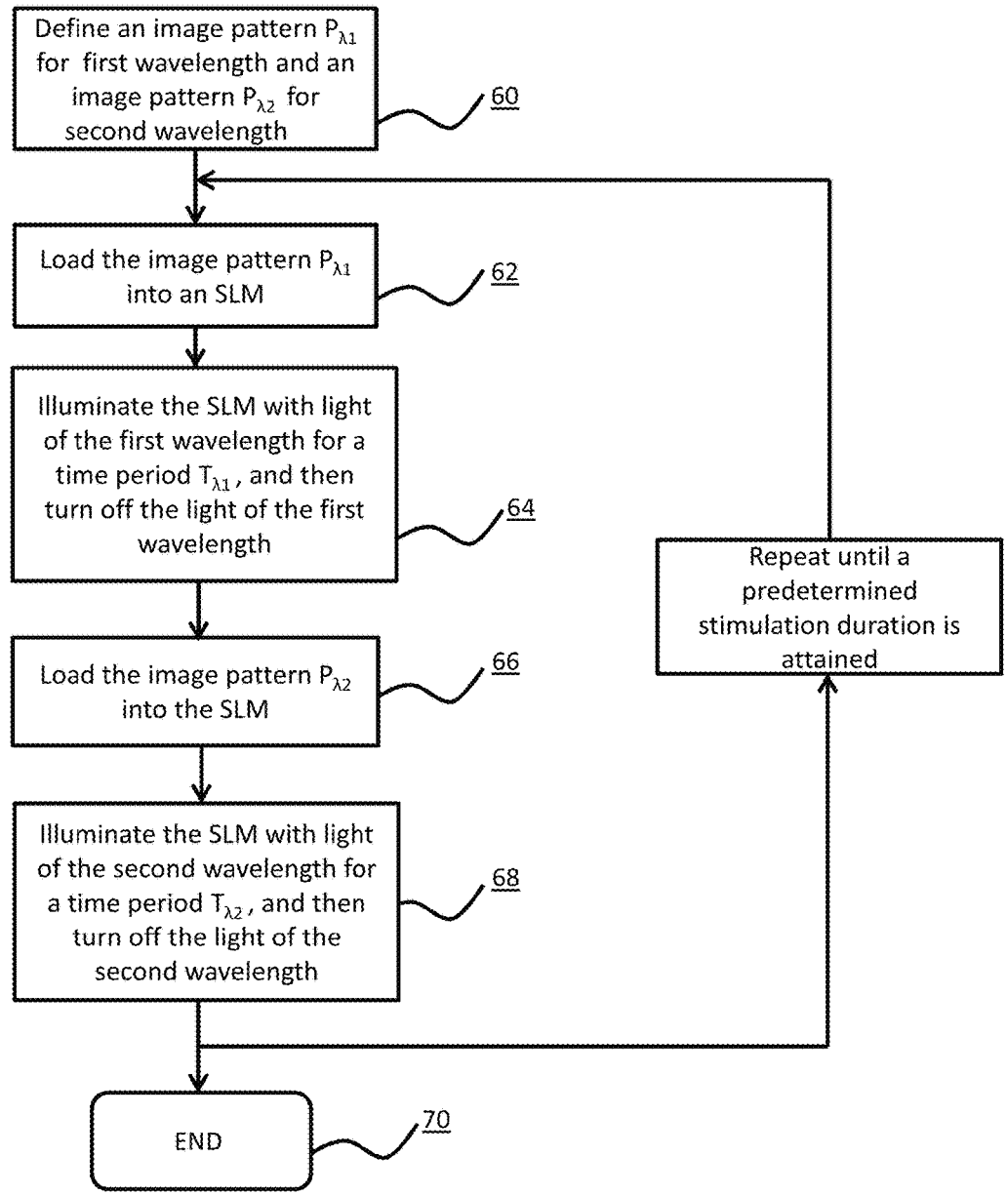
FIG. 3 is a flow chart showing an exemplary set of functions carried out using the optical illumination system of FIG. 1A.

Various embodiments and aspects of the invention will be described with reference to details discussed below, and the accompanying drawings will illustrate the various embodiments. The following description and drawings are illustrative of the invention and are not to be construed as limiting the invention.

In this regard, different arrangements described herein are provided by way of example only, and other arrangements and elements can be added or used instead and some elements may be omitted altogether. Also, those skilled in the art will appreciate that many of the elements described herein are functional entities that may be implemented as discrete components or in conjunction with other components, in any suitable combination and location, and various functions could be carried out by software, firmware and/or hardware.

FIG. 1A depicts an optical illumination system 10 in which an illustrative embodiment of the present invention could be carried out.

As shown in FIG. 1A, the optical illumination system 10 comprises a modulating driver 12 coupled to a light source 14 configured to illuminate an SLM 16 with light. Although FIG. 1 shows a direct light path 18 between the light source 14 and the SLM 16, any suitable optical component(s) may coupled between the light source 14 and the SLM 16 in the light path 18 to direct light output by the light source 14 onto the SLM 16.

The optical illumination system 10 further comprises a microscope system 20 (also referred to as "Microscope" in FIG. 1) that receives an image output by the SLM 16 via an optical path 22. Although not explicitly shown in FIG. 1A, it should be understood the optical path 22 between an output of the SLM 16 and an input into the microscope system 20 may include additional optical component(s) (e.g., multiple lense(s)) in order to efficiently couple an SLM image light into the microscope system 20. Further, the SLM 16 may be positioned appropriately with respect to the input to the microscope system 20 to direct light into the input to the microscope system 20.

As further shown in FIG. 1A, the SLM image light input to the microscope system 20 passes through an internal optical path 24 within the microscope system 20 before being projected via an objective lens 26 onto a specimen 30. In the illustrative embodiment, the SLM 16 and the specimen 30 are in conjugate planes. As illustrated, the internal optical path 24 of the microscope system 20 may include a number of lenses 28 and beam splitter(s) 32 that can manipulate the SLM image light as needed to project it onto the specimen 30. Preferably, the specimen 30 is a biological specimen, such as neuron(s) or cell(s), that can be optically stimulated through suitable light illumination.

Note, however, that the microscope system 20 and its internal arrangement is provided for illustrative purposes only, and it may be possible to use other optical system(s) instead. For example, it may be possible to use another optical system arranged to function as a microscope and configured in accordance with principles of the present disclosure.

In accordance with the illustrative embodiment, the light source 14 is configured to illuminate the SLM 16 with light of a first wavelength (λ1) and light of a second wavelength (λ2) that is different from the first wavelength. In the illustrative embodiment, the first wavelength may be a shorter wavelength associated with a first color (e.g., a wavelength of approximately 450-495 nm corresponding to a blue color), while the second wavelength may be a longer wavelength associated with a second color (e.g., a wavelength of approximately 620-740 nm corresponding a red color) different from the first color. Alternatively, the first wavelength could be a longer wavelength, while the second wavelength could be a shorter wavelength.

The modulating driver 12 is configured to modulate the light source 14 by turning the light source 14 on or off. The light source 14 may be any suitable one or more sources of light, light-emitting diode(s) (LED(s)) (as generally depicted in FIG. 1A) or solid-state laser device(s). For example, the light source 14 may be a single light source capable of generating light of two or more different wavelengths. Alternatively, the light source 14 may be multiple light sources each individually generating light of a given wavelength. Further, in the illustrative embodiment, the light from the light source 14 may pass through any suitable optical component(s), such as optical filters, to derive light of desirable wavelengths.

To illustrate, the light source 14 may be two or more light sources producing separate light beams with different wavelengths (e.g., a blue light beam and a red light beam), and a beam combiner can be disposed in the light path 18 between the light source 14 and the SLM 16 to combine those separate light beams and direct them onto the SLM 14. Those skilled in the art will appreciate that the beam combiner can be, e.g., a dichroic beam splitter that can separate multiple light beams into separate light beams of different wavelengths but can also be configured to function as a combiner to combine light beams of different wavelengths.

In the illustrative embodiment, light output by the light source 14, such as the light of the first wavelength or the light of the second wavelength, is directed onto the SLM 16 that, in turn, can modulate each light independently. More specifically, the SLM can modulate each light in accordance with an associated image pattern loaded into the SLM 16. Generally, the image pattern loaded into the SLM 16 represents an image data according to which the SLM 16 will modulate light input to the SLM 14 to produce a desired output image. Preferably, the SLM 16 is a digital micromirror device ("DMD"). However, in another embodiment, the SLM 16 may be, for instance, in the form of a ferroelectric liquid crystal display.

As those skilled in the art will recognize, a typical DMD will include a large number of microscopic mirrors that each represent an individual pixel and can be controlled to be either in an "on" state or an "off" state in accordance with binary data. The mirrors/pixels are arranged in a two-dimensional array of rows and columns, and the DMD can modulate incoming light in accordance with an image data to output a desired image. Further, the dimensions of the pixel array will depend on the resolution of the DMD (e.g., 1024 rows by 768 columns).

Although not shown, one skilled in the art will recognize that the SLM 16, such as a DMD, will be configured with suitable hardware, processing unit(s), memory, software/logic modules, input lines, buses, and the like, to process an image pattern input into the SLM 16 and load it into appropriate portions of the pixel array of the SLM 16. In this regard, data represented by the image pattern can be loaded to the pixel array in any suitable fashion, such as on a row-by-row basis.

As a general matter, in accordance with the illustrative embodiment, the SLM 16 produces an output image that is projected onto a specimen receiving optical stimulation (e.g., the specimen 30) via a suitable optical system, such as the microscope system 20. The output image projected onto the specimen is based on multiple images, and in particular, multiple interleaved images that are of different wavelengths or colors from each other. FIG. 1B shows one example of an output image 40 projected onto the specimen 30, where the output image 40 contains two independent images, namely, an image 42 associated with the first wavelength (e.g., an image of a first color, such as blue) and an image 44 associated with the second wavelength (e.g., an image of a second color, such as red). As such, the output image 40 has a first illuminated area (e.g., a blue area) corresponding to the image 42 and a second illuminated area corresponding to the image 44 (e.g., a red area) that are illuminating the specimen 30.

More specifically, in the illustrative embodiment, the SLM 16 is illuminated by light of two different wavelengths in an alternating manner. The illumination is preferably synchronized with a frame rate of the SLM 16, where the frame rate of an SLM generally corresponds to a rate at which the SLM produces an image, or a frame. FIG. 2 depicts an example of such interleave scheme in which a light pulse 50 associated with the first wavelength and a light pulse 52 associated with the second wavelength are being alternated every 0.1 ms.

In particular, if the SLM 16 has a frame rate of 10,000 frames per second (or 0.1 ms per frame), then during the first frame, the SLM 16 will be illuminated by the light of the first wavelength (e.g., a wavelength corresponding to a blue color) for 0.1 ms to produce an image associated with the first wavelength (e.g., the image 42). During the second frame, the SLM 16 will be illuminated by the light of the second wavelength (e.g., a wavelength corresponding to a red color) for 0.1 ms to produce an image associated with the second wavelength (e.g., the image 44). During the third frame, the SLM 16 will again be illuminated by the light of the first wavelength to produce the image 42, and so forth. As such, the SLM 16 is illuminated by the light of the two wavelengths in an alternating manner during consecutive time periods to produce corresponding images that are interleaved by 0.1 ms.

Further, in accordance with the illustrative embodiment, a time period (e.g., 0.1 ms) during which light of a given wavelength is turned on, or in an on state, is shorter than a response time of the specimen 30 so that the specimen 30 is not able to detect a time delay between successive images. As used herein, the term "response time" generally refers to a time that takes for an element, a functional unit, a system, a network, etc., to react/respond to a given input or stimulus.

In effect, in the above example of FIGS. 1B and 2, the images 42 and 44 in the output image 40 would appear to the specimen 30 as being projected at the same time for a total time duration of 0.5 ms using three frames for each wavelength/color. Therefore, the specimen 30 can be optically stimulated with each color for a duration of 0.5 ms.

Various features of the present invention will be now explained in greater detail with reference to a flow chart of FIG. 3 illustrating an exemplary set of functions that could be carried out using the optical illumination system 10 for optical stimulation of the specimen 30, for instance.

As shown in FIG. 3, at step 60, a user defines an image pattern $P_{\lambda 1}$ associated with the first wavelength and an image pattern $P_{\lambda 2}$ associated with the second wavelength. As noted above, in the illustrative embodiment, the first wavelength may be a shorter wavelength associated with the first color, such as blue, and the second wavelength may be a longer wavelength associated with the second color, such as red.

At step 62, the image pattern $P_{\lambda 1}$ is loaded into the SLM 16. Upon loading the image pattern $P_{\lambda 1}$ into the SLM 16, at step 64, the SLM 16 is illuminated with the light of the first wavelength from the light source 14 for a time period $T_{\lambda 1}$, such as a time period synchronized with an SLM frame rate (e.g., 0.1 ms, as in the example above). The light of the first wavelength is then turned off, such as by turning off the light source 14 via the modulating driver 12. Note that the loading time of the image pattern $P_{\lambda 1}$ will typically be almost instantaneous, and thus can be disregarded.

During the time period $T_{\lambda 1}$, the light of the second wavelength is turned off, or in an off state. In this regard, the modulating driver 12 can be configured to control the light source 14 to keep the light of the second wavelength in the off state. Further, a level of light intensity $I_{\lambda 1}$ associated with the first wavelength can be controlled independently at the light source 14.

At step 66, an image pattern $P_{\lambda 2}$ is loaded into the SLM 16. Upon loading the image pattern $P_{\lambda 2}$ into the SLM 16, at step 68, the SLM 16 is illuminated with the light of the second wavelength from the light source 14 for a time period $T_{\lambda 2}$, such as a time period synchronized with an SLM frame rate (e.g., 0.1 ms, as in the example above). The light of the second wavelength is then turned off, such as by turning off the light source 14 via the modulating driver 12. Note that the loading time of the image pattern $P_{\lambda 2}$ will typically be almost instantaneous, and thus can be disregarded.

During the time period $T_{\lambda 2}$, the light of the first wavelength is turned off, or in an off state. In this regard, the modulating driver 12 can be configured to control the light source 14 to keep the light of the first wavelength in the off state. Further, a level of light intensity $I_{\lambda 2}$ associated with the second wavelength can be controlled independently at the light source 14.

As shown in FIG. 3, the steps 62-68 are iteratively repeated until a predetermined stimulation duration is attained. Then, the process ends at step 70.

In the illustrative embodiment, the steps 62-68 are carried out, in that order, a total of N times. The time period $T_{\lambda 1}$ and the time period $T_{\lambda 2}$ are substantially equal to each other and constant in duration at every iteration. In this case, the predetermined stimulation duration associated with the first wavelength and the second wavelength is computed according to the following formula:

Stimulation Duration=$(2N-1)*T_\lambda$, where $T_\lambda$, is an illumination time period associated with wavelengths λ1 and λ2.

To illustrate, as shown in FIG. 2, the light pulse 50 associated with the first wavelength and the light pulse 52 associated with the second wavelength are alternated for N=3 times during a period of six frames. Given that a duration (or width) of each light pulse is 0.1 ms, a total stimulation duration is ((2*3)−1)*0.1 ms, or 0.5 ms.

Further, as noted above, in accordance with the illustrative embodiment, each of the time period $T_{\lambda 1}$ and the time period $T_{\lambda 2}$ is shorter than a response time of the specimen 30 so that the specimen is not able to detect a time delay between the light pulses of the two wavelengths or colors. In one example, the time period $T_{\lambda 1}$, or a duration of the time pulse associated with the first wavelength, and the time period $T_{\lambda 2}$, or a duration of the time pulse associated with the second wavelength, could be each equal to or greater than about 67% of the response time but less than 100% of the response time. In this case, 67% corresponds to the response time being about 1.5 times longer than the time period $T_{\lambda 1}$ and the time period $T_{\lambda 2}$. In another example, the time period $T_{\lambda 1}$ and the time period $T_{\lambda 2}$ could be each equal to or less than about 33% of the response time. In this case, 33% corresponds to the response time being about 3 times longer than the time period $T_{\lambda 1}$ and the time period $T_{\lambda 2}$. However, it should be understood that these examples are not limiting, and other examples may be possible as well.

Accordingly, in the example of FIGS. 1B and 2, the specimen 30 (e.g. neuron(s)) under study would be too slow to respond to the individual 0.1 ms light pulses, and hence the specimen 30 will effectively see a first-color illumination pattern (e.g., the image 42) and a second-color illumination pattern (e.g., the image 44) at the same time for a period of 0.5 ms. Advantageously, a simultaneous two-color stimulation pattern with a time duration of 0.5 ms is achieved by using three frames for each color. The 0.1 ms delay between the two colors is immaterial for many experiments involving, e.g., a neural network because the neural network is not fast enough to feel this short delay. However, it should be understood that a time period of 0.1 ms is used for the purpose of example only, and time periods of other durations may be used instead based on a type of a specimen and its response time.

Note that, as shown in FIG. 2, a level of light intensity associated with the light pulses 50 of the first wavelength and the light pulses 52 of the second wavelength are different. Thus, not only two patterns of different colors but also of different light intensities can be produced and illuminated onto the specimen 30. In this case, the level of light intensity for each wavelength can be independently controlled at the light source 14. Further, although the above example assumes N=3 times, one can vary N accordingly to attain a desired stimulation period. For example, if N was increased to 4 times, the stimulation duration would be 0.7 ms (i.e., ((2*4)−1)*0.1 ms).

With a benefit of the present disclosure, one can simultaneously illuminate certain portion(s) of a specimen with light of one color and other portion(s) of the specimen with a light of another color using only a single SLM. As such, the specimen can be optically stimulated with two independent colors for a desired stimulation duration. Also, the present disclosure provides a way to carry out optical stimulation without introducing an undesirable time-dependence that would typically occur with traditional displays due to response times of specimens, such as neurons.

Note that, in the above examples, the image pattern $P_{\lambda 1}$ and the image pattern $P_{\lambda 2}$ can be configured accordingly to generate desired image shapes/patterns for each color. Further, although the example of FIG. 1B shows the images 42 and 44 as having different shapes from each other and occupying different areas in the output image 40, the image pattern $P_{\lambda 1}$ and the image pattern $P_{\lambda 2}$ can be configured to have the same patterns that overlap each other either fully or partially to produce an illuminated area that is a mixture of both colors.

Further, although FIG. 1A-3 describe one illustrative embodiment of the present disclosure, variations are possible.

For example, although the above description assumes two wavelengths corresponding to two independent colors, methods of the present invention can be applied to three or more wavelengths. For example, the process of FIG. 3 may be extended to three different wavelengths. As such, the output image 40 may be produced by alternating SLM frames respectively corresponding to three different wavelengths to produce illumination patterns of three different colors.

Further, although in the above description the terms "first wavelength" and "second wavelength" are used respectively in reference to single wavelengths (e.g., a wavelength associated with a particular color (e.g., red or blue)), it should be understood that each of these terms can also represent a band of wavelengths rather than a single wavelength. To illustrate, in one alternative embodiment, the first wavelength can represent a first band of wavelengths, while the second wavelength can represent a second band of wavelengths different from the first band of wavelengths.

Also note that, the SLM frames associated with a particular wavelength do not have to be of identical patterns. Similarly, durations and intensities of light pulses of the same wavelength do not have to be identical either.

Therefore, to generalize in the context of FIG. 3 for instance, during each iteration of the steps 62-68, an image pattern $P_\lambda(i)$ associated with a given wavelength $\lambda$ is loaded into the SLM 16 while light of the given wavelength is illuminated at an intensity level $I_\lambda(i)$ for a time period $T_\lambda(i)$, where the symbol i is an integer number (e.g., i=1, 2, . . . , n) denoting that the image pattern $P_\lambda$, the intensity level $I_\lambda$, and the time period $T_\lambda$ can take on different values from one SLM frame to another, depending on the value of symbol i.

Advantageously, the above-noted flexibilities can be used to generate light intensity variations (or, generally, grayscales) within a stimulation pattern. For example, an image of a given color (e.g., a blue image) can be defined to have a 100%-intensity region (or a region where light intensity is at a full level of 100%) and a region of lower intensity, such as a 33.3%-intensity region (or a region where light intensity is at a lower level of 33%).

In this case, in the 100%-intensity region, pixels within that region and blue illumination would be fully turned on during all three blue SLM frames. In the 33.3%-intensity region, pixels within that region and the blue illumination would be fully turned on during the first blue frame. During the second and third blue frames, the pixels in the 33.3% region would be turned off. This results in an illumination region with 33.3% intensity (grayscale).

For example, assuming blue (B) and red (R) light pulses occurring alternately during six consecutive SLM frames, a sequence of light pulses would be B1, R, B2, R, B3, R. In this example, image patterns corresponding to the B1, B2, and B3 pulses are not identical. In an image pattern corresponding to the B1 pulse, pixels in the 100%-intensity region and the 33%-intensity region are defined to be on. In image patterns corresponding respectively to the B2 and B3 pulses, the pixels in the 100%-intensity region are defined to be on, but the pixels in the 33%-intensity region are defined to be off.

When blue light is illuminated onto an SLM during a first blue frame, the pixels in both regions would emit the blue light. However, when the blue light is illuminated onto the SLM during second and third blue frames, the blue light would be only emitted by the pixels in the 100%-intensity region since the pixels in the 33%-intensity region are turned off. As a result, during all three blue frames, the pixels in the 33%-intensity region have effectively only one third (⅓) of the intensity compared to the pixels in the 100%-intensity region.

Figure 4:
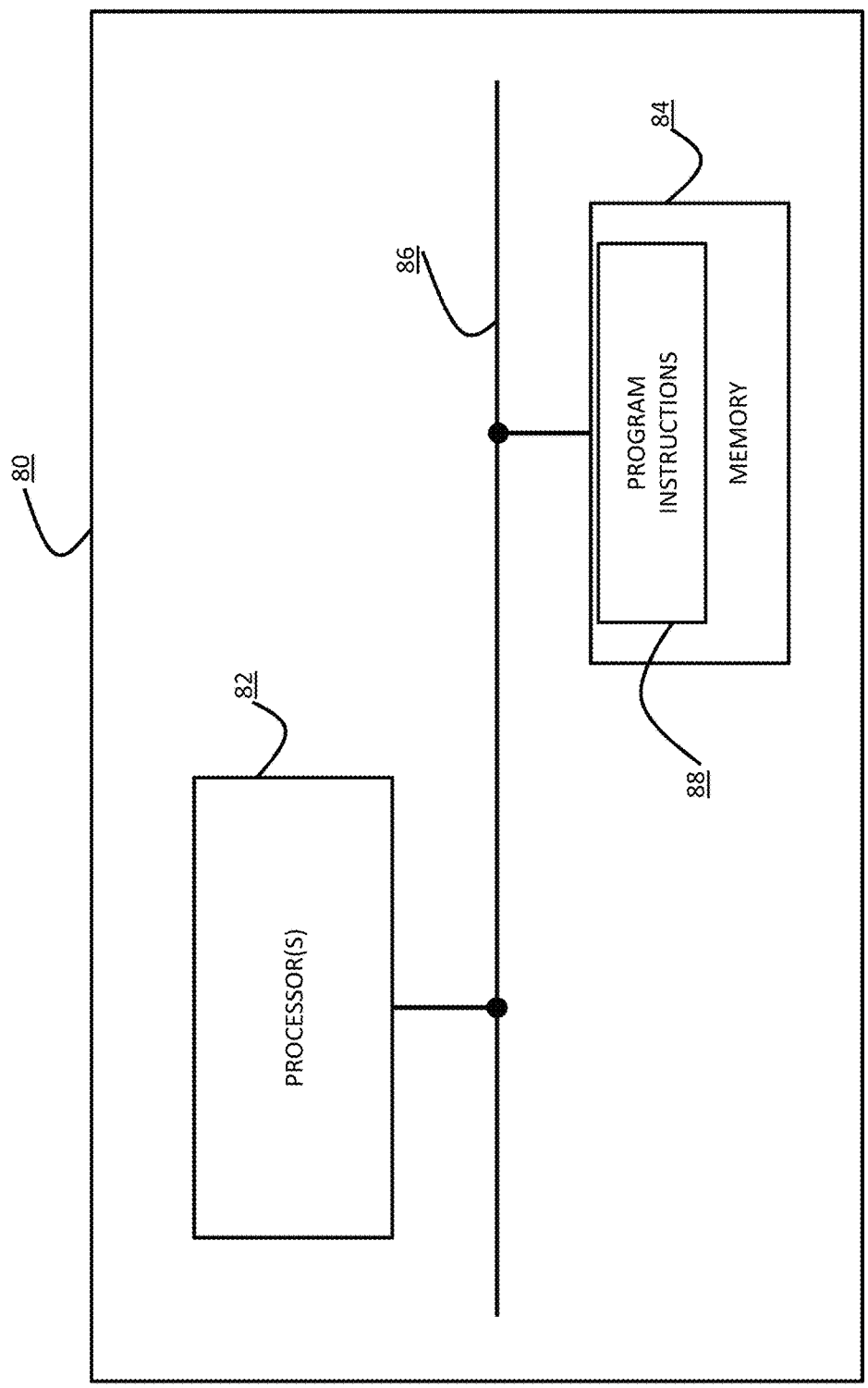
FIG. 4 illustrates a processing system in accordance with one embodiment.

Various functions described herein, such as in FIG. 3 above, could be carried out by a processing system 80, as shown in FIG. 4. The system 80 includes at least one processor 82 and memory 84, coupled together via a bus 86. The processing system 80 may be, for example, incorporated in a separate controller controlling the element(s) of the optical illumination system 10 (e.g., the SLM 16, the modulating driver 12, etc.) or its components may be distributed fully or partially across the element(s) of the optical illumination system 10. Various examples are possible.

In one embodiment, the processor(s) 82 may be dedicated processor(s) or general purpose processor(s) configured to execute computer-readable program code. The memory 84 may be volatile or non-volatile non-transitory computer-readable medium or media, now known or later developed. The memory 84 may hold program logic comprising program instructions 88 (e.g., machine language instructions) executable by the processor(s) 82 to carry out various functions described herein. Additionally, the memory 84 may store any other data, such as data used by the processor(s) 82 in the execution of the program instructions 88. However, any additional data may also be held in other data storage location(s) separate from the memory 84.

Further, although not shown in FIG. 4, the processing system 80 may include a number of interfaces, such as user interface(s), communication interface(s) (e.g., an interface for communicating data to/from the memory 84, etc.), and/or the like. Also, other elements (e.g., modules, input lines, buses, etc.) may be included as well.

As used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B are satisfied by any one of the following: A is true (or present) and B is false (or not present), A is false (or not present) and B is true (or present), and both A and B are true (or present).

The terms "a" or "an," as used herein, are defined as one or more than one. The term "plurality," as used herein, is defined as two or more than two. The term "another," as used herein, is defined as at least a second or more.

The invention can be implemented in numerous ways, including as a process, an apparatus, and a system. In this specification, these implementations, or any other form that the invention may take, may be referred to as techniques. In general, the order of the connections of disclosed apparatus may be altered within the scope of the invention.

The present invention has been described in particular detail with respect to some possible embodiments. Those skilled in the art will appreciate that the invention may be practiced in other embodiments. First, the particular naming of the components, capitalization of terms, the attributes, data structures, or any other programming or structural aspect is not mandatory or significant, and the mechanisms that implement the invention or its features may have different names, formats, or protocols. Further, the system may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead be performed by a single component. An ordinary artisan should require no additional explanation in developing the methods and systems described herein but may nevertheless find some possibly helpful guidance in the preparation of these methods and systems by examining standard reference works in the relevant art.

These and other changes can be made to the invention in light of the above detailed description. In general, in the following claims, the terms used should not be construed to limit the invention to the specific embodiments disclosed in the specification and the claims, but should be construed to include all methods and systems that operate under the claims set forth herein below. Accordingly, the invention is not limited by the invention, but instead its scope is to be determined entirely by the following claims.

The invention claimed is:

1. A method for driving an optical device for optical stimulation, the method comprising:
    (a) providing an image pattern $P_{\lambda 1}(i)$ associated with light of a first wavelength and an image pattern $P_{\lambda 2}(i)$ associated with light of a second wavelength to be loaded into a spatial light modulator (SLM), the first and second wavelengths being different from each other;
    (b) providing a light source coupled to a driver and configured to output the light of the first wavelength and the light of the second wavelength;
    (c) upon loading the image pattern $P_{\lambda 1}(i)$ into the SLM, illuminating the SLM with the light of the first wavelength at an intensity level $I_{\lambda 1}$ for a time period $T_{\lambda 1}(i)$ before turning off the light of the first wavelength via the driver modulating the light source, the light of the second wavelength being in an off state during the time period $T_{\lambda 1}(i)$;
    (d) upon loading the image pattern $P_{\lambda 2}(i)$ into the SLM, illuminating the SLM with the light of the second wavelength at an intensity level $I_{\lambda 2}(i)$ for a time period $T_{\lambda 2}(i)$ before turning off the light of the second wavelength via the driver modulating the light source, the light of the first wavelength being in an off state during the time period $T_{\lambda 2}(i)$; and
    (e) iteratively repeating the step (c) and the step (d), in that order, until a predetermined stimulation duration of a biological specimen is attained, the combination of a plurality of shorter pulses from the first wavelength generating a response from the biological specimen, each pulse individually from the first wavelength being insufficient to generate the response from the biological specimen;
    wherein the symbol i is an integer number from 1 to N and the symbol N is an integer number greater than 1; and
    wherein the time period $T_{\lambda 1}(i)$ is shorter than a response time of a specimen that is being optically stimulated.

2. The method of claim 1, wherein the specimen includes a neuron.

3. The method of claim 1, wherein the time period $T_{\lambda 1}(i)$ is equal to or greater than about 67% of the response time but less than 100% of the response time.

4. The method of claim 1, wherein the time period $T_{\lambda 1}(i)$ is equal to or less than about 33% of the response time.

5. The method of claim 1, wherein the time period $T_{\lambda 2}(i)$ is shorter than a response time of a biological specimen that is being optically stimulated.

6. The method of claim 5, wherein the specimen includes a neuron.

7. The method of claim 5, wherein the time period $T_{\lambda 2}(i)$ is equal to or greater than about 67% of the response time but less than 100% of the response time.

8. The method of claim 5, wherein the time period $T_{\lambda 2}(i)$ is equal to or less than about 33% of the response time.

9. The method of claim 1, wherein the time period $T_{\lambda,1}(i)$ and the time period $T_{\lambda,2}(i)$ are substantially equal to each other and constant in duration every time the steps (c) and (d) are carried out.

10. The method of claim 9, wherein when (a) the time period $T_{\lambda,1}(i)$ and the time period $T_{\lambda,2}(i)$ are equal to $T_\lambda$ and (b) the steps (c) and (d) are carried out N times, the predetermined stimulation duration is computed based on the following equation:

Stimulation Duration=$(2N-1)*T_\lambda$.

11. The method of claim 1, wherein the first wavelength comprises a shorter wavelength relative to the second wavelength.

12. The method of claim 1, wherein the second wavelength comprises a longer wavelength relative to the first wavelength.

13. The method of claim 1, wherein the first wavelength corresponds to a first color and the second wavelength corresponds to a second color different from the first color.

14. The method of claim 1, wherein in response to the steps (c) through (e), the SLM produces an output image containing a first image associated with the first wavelength and a second image associated with the second wavelength.

15. The method of claim 14, further comprising:
(f) projecting the output image onto a specimen for the predetermined stimulation duration.

16. The method of claim 15, wherein:
each of the time period $T_{\lambda,1}(i)$ and the time period $T_{\lambda,2}(i)$ is shorter than a response time of the specimen.

17. The method of claim 16, wherein the first and second images in the output image are output to appear to the biological specimen as being projected simultaneously for the predetermined stimulation duration.

18. A method for driving an optical device for optical stimulation, the method comprising:
providing a driver, a light source coupled to the driver, and a spatial light modulator (SLM) in optical communication with the light source, the SLM is configured to independently (i) modulate light of a first wavelength in accordance with a first predefined image pattern to be loaded into the SLM and (ii) modulate light of a second wavelength in accordance with a second predefined image pattern to be loaded into the SLM, the first and second wavelengths being different from each other; and
carrying out the following steps (1) and (2), in that order, a number of times until a predetermined stimulation duration of a biological specimen is attained:
(1) upon loading the first predefined image pattern into the SLM, illuminating the SLM with the light of the first wavelength for a first time period before turning off the light of the first wavelength via the driver modulating the light source, the light of the second wavelength being in an off state during the first time period, and
(2) upon loading the second predefined image pattern into the SLM, illuminating the SLM with the light of the second wavelength for a second time period before turning off the light of the second wavelength via the driver modulating the light source, the light of the first wavelength being in an off state during the second time period;
wherein each of the first time period and the second time period is shorter than a response time of the specimen, the combination of a plurality of shorter pulses from the first wavelength generating a response from the biological specimen, each pulse individually from the first wavelength being insufficient to generate the response from the biological specimen.

19. The method of claim 18, wherein the light of the first wavelength is illuminated at a first intensity level.

20. The method of claim 18, wherein the light of the second wavelength is illuminated at a second intensity level.

21. The method of claim 18, wherein:
the first and second time periods are both equal to $T_\lambda$,
the number of times is N, and
the predetermined stimulation duration is computed based on the following equation:

Stimulation Duration=$(2N-1)*T_\lambda$.

22. The method of claim 18, further comprising:
projecting, onto the specimen, a first image light produced by the SLM in accordance with the first predefined image pattern and a second image light produced by the SLM in accordance with the second predefined image pattern.

23. The method of claim 22, wherein the specimen includes a neuron.

24. The method of claim 18, wherein the first time period and the second time period are each synchronized with a frame rate of the SLM.

25. The method of claim 18, wherein:
at least one of the first predefined image pattern and the second predefined image pattern defines an image having a first region of a first light intensity and a second region of a second light intensity, a level of the second light intensity being lower than that of the first light intensity.

26. The method of claim 25, wherein:
the first predefined image pattern defines the image having the first region and the second region,
the steps (1) and (2) are carried out at least twice during consecutive SLM frames,
in a first SLM frame, the step (1) is carried out, pixels in the first region being turned on and pixels in the second region being turned on,
in a second SLM frame, the step (2) is carried out,
in a third SLM frame, the step (1) is carried out, the pixels in the first region being turned on and the pixels in the second region being turned off, and
in a fourth SLM frame, the step (2) is carried out.

27. The method of claim 18, wherein the steps (1) and (2) are alternately carried out at least twice during consecutive SLM frames.

28. A method for driving an optical device for optical stimulation, the method comprising:
providing a driver, a light source coupled to the driver, and a spatial light modulator (SLM) in optical communication with the light source, the SLM is configured to independently (i) modulate light of a first wavelength in accordance with a first predefined image pattern to be loaded into the SLM and (ii) modulate light of a second wavelength in accordance with a second predefined image pattern to be loaded into the SLM, the first and second wavelengths being different from each other; and
carrying out the following steps (1) and (2), in that order, a number of times until a predetermined stimulation duration is attained:
(1) upon loading the first predefined image pattern into the SLM, illuminating the SLM with the light of the first wavelength for a first time period before turning off the light of the first wavelength via the driver modulating the light source, and
(2) upon loading the second predefined image pattern into the SLM, illuminating the SLM with the light of the second wavelength for a second time period before turning off the light of the second wavelength via the driver modulating the light source;
wherein the first image light and the second image light are output to appear to a biological specimen as being projected simultaneously for the predetermined stimulation duration;
wherein each of the first time period and the second time period is shorter than a response time of the specimen, the combination of a plurality of shorter pulses from the first wavelength generating a response from the biological specimen, each pulse individually from the first wavelength being insufficient to generate the response from the biological specimen.

* * * * *